US008945938B2

(12) United States Patent
Knop (10) Patent No.: US 8,945,938 B2
(45) Date of Patent: Feb. 3, 2015

(54) COMPOSITION, DEVICE AND METHOD FOR COLORIMETRIC DETECTION OF AN ANALYTE USING IMPRINTED POLYMERS AND PHOTOCHROMIC SWITCH MOLECULES

(75) Inventor: Richard H. Knop, Beach Park, IL (US)

(73) Assignee: Medtech Detect, LLC, Buffalo Grove, IL (US)

(\*) Notice: Subject to any disclaimer, the term of this patent is extended or adjusted under 35 U.S.C. 154(b) by 344 days.

(21) Appl. No.: 13/504,719

(22) PCT Filed: Oct. 26, 2010

(86) PCT No.: PCT/US2010/054109
§ 371 (c)(1),
(2), (4) Date: Apr. 27, 2012

(87) PCT Pub. No.: WO2011/053587
PCT Pub. Date: May 5, 2011

(65) Prior Publication Data
US 2012/0214252 A1    Aug. 23, 2012

Related U.S. Application Data

(60) Provisional application No. 61/256,618, filed on Oct. 30, 2009.

(51) Int. Cl.
*G01N 21/00* (2006.01)
*G01N 33/542* (2006.01)
(52) U.S. Cl.
CPC .......... *G01N 33/542* (2013.01); *G01N 2600/00* (2013.01)
USPC ...................................... 436/164; 422/82.05

(58) Field of Classification Search
None
See application file for complete search history.

(56) References Cited

PUBLICATIONS

International Search Report and Written Opinion under date of mailing of Dec. 16, 2012 in connection with PCT/US2010/054109.
Kato R et al: "A thiourea-based chromoionophore for selective binding and sensing of acetate", Tetrahedron Letters, Elsevier, Amsterdam, NL, vol. 42, No. 30, Jul. 23, 2001; pp. 5053-5056, XP004250176, ISSN: 0040-4039, DOI: DOI:10.1016/S0040-4039(01)00916-9.
Manesiotis P et al: "An enantioselective imprinted receptor for Z-glutamate exhibiting a binding induced color change", Chemical Communications—Chemcom, Royal Society of Chemistry, GB, Jan. 1, 2004, pp. 2278-2279, XP002995329, ISSN: 1359-7345, DOI: DOI:10.1039/B407870E.
Sakata T et al: "Family of site-selective molecular optical switches", Journal of Organic Chemistry Mar. 18, 2005 American Chemical Society US, vel. 70, No. 6, Mar. 18, 2005, pp. 2009-2013, XP002612048, DOI: DOI:10.1021/J00482070.

(Continued)

*Primary Examiner* — Robert Xu
(74) *Attorney, Agent, or Firm* — Quarles & Brady, LLP (57) ABSTRACT

The invention provides various compositions, devices, and methods useful for detecting an analyte by colorimetric readout. The compositions and devices include polymers constructed to have pores specifically imprinted to provide for capture of an analyte in the pores; nanoparticles layered on the polymers; and photochromic optical switch molecules coated on the nanoparticles. Capture of the analyte in the pores of the polymer results in a change in the spatial relation of the nanoparticles layered on the polymer, which in turn causes the photochromic optical switch molecules coated thereon to undergo a change in energy state corresponding to a visible change in the optical spectra of the photochromic optical switch molecules.

5 Claims, 3 Drawing Sheets

Nano Material Such as Gold

*C* Multi-Chromophoric Unit

(56) References Cited

PUBLICATIONS

Raymo Francisco M et al: "Electron and energy transfer modulation with photochromic switches.", Chemical Society Reviews Apr. 2005 LNKD—PUBMED:15778766, vel. 34, No. 4, Apr. 2005, pp. 327-336, XP002612049, ISSN: 0306-0012.

Matsui J et al: "Composite of Au Nanoparticles and Molecularly Imprinted Polymer As a Sensing Material", Analytical Chemistry, American Chemical Society, US, vol. 76, No. 5, Mar. 1, 2004, pp. 1310-1315, XP001196700, ISSN: 0003-2700, DOI: DOI:10.1021/AC034788Q.

Shipway An et al: "Electronically transduced molecular mechanical and information functions on surfaces.", Accounts of Chemical Research Jun. 2001 LNKD—PUBMED:11412079, vel. 34, No. 6, Jun. 2001, pp. 421-432, XP002612050, ISSN: 0001-4842.

COMPOSITION, DEVICE AND METHOD FOR COLORIMETRIC DETECTION OF AN ANALYTE USING IMPRINTED POLYMERS AND PHOTOCHROMIC SWITCH MOLECULES

CROSS-REFERENCE TO RELATED APPLICATIONS

This application represents the national phase entry under 35 U.S.C. 371 of PCT/US2010/054109 filed Oct. 26, 2010, which claims the benefit of U.S. Provisional Application No. 61/256,618, filed Oct. 30, 2009, which is incorporated by reference herein.

STATEMENT REGARDING FEDERALLY SPONSORED RESEARCH OR DEVELOPMENT

Not Applicable.

FIELD OF THE INVENTION

The present invention relates generally to analyte sensors and molecularly imprinted polymers (MIPs). In particular, the invention is related to various compositions, devices and methods useful for detecting an analyte by colorimetric readout.

BACKGROUND OF THE INVENTION

Current commercial methods for drug or other analyte detection in solutions such as urine primarily involve antibody staining systems attached to Whatman filter paper. Such antibody staining systems are generally targeted to specific analytes. An exemplary use for such a system is to dip the antibody drug detection device into a sample and observe a color change correlating with the presence or absence of the analyte. A difficulty in using these systems is that they often yield negative results. For example, such systems may give a color change when the corresponding analyte is not present. They also do not give a permanent color change.

Molecularly imprinted polymers are polymers that have been traditionally used to filter and purify compounds during production processes. The polymers are formed in the presence of a molecule that is extracted afterwards, thus leaving cavities complementary to the extracted molecule behind. These polymers show a certain chemical affinity for the extracted molecule and thus can be used to fabricate sensors.

Creating a molecularly imprinted polymer that can be used as a biosensor capable of producing a permanent and positive color change for detection of an analyte would fulfill a long held need and be a large improvement over existing antibody-based drug detection systems.

SUMMARY OF THE INVENTION

The present invention combines two different technologies: nano-technology-biosensor detection and guest-host organic chromophores for measuring spectral characteristics of delocalized electrons within or associated with any molecular recognition device as a colorimetric optical readout. The combined technologies provide platforms for a biosensor reaction that can be used to detect the presence or absence of a substance of interest. The detection is based on the spatial changes of surface elemental or metal nano and internal analyte components relative to each other. This biosensing paradigm is sufficient to detect a reaction in which a guest host paradigm is the underlying mechanism.

Accordingly, the present invention provides compositions, devices and methods for detecting the presence or absence of a substance, chemical, or molecule of interest (herein termed "analyte") via an indicator mechanism. This indicator mechanism is secured to at least one recognition site, whereby presence of the substance, chemical, or molecule of interest on the recognition site causes a permanent and detectable change in an aspect of the composition or device. The indicator mechanism readout is colorimetric. The color readout preferably stays permanent over the lifetime of the composition or device and does not change once the item of interest has been detected.

In one aspect, the invention provides a composition for use in detecting an analyte in a sample by colorimetric optical readout, comprising: (a) a polymer having pores specifically imprinted to provide for capture of an analyte in said pores; (b) nanoparticles layered on said polymer; and (c) photochromic optical switch molecules coated on said nanoparticles, wherein capture of the analyte in the pores of the polymer results in a change in the spatial relation of the nanoparticles layered on the polymer, said change in spatial relation of the nanoparticles causing the photochromic optical switch molecules coated thereon to undergo a change in energy state which corresponds to a visible change in optical spectra of said photochromic optical switch molecules, thereby providing detection of the analyte by colorimetric optical readout.

In another aspect, the invention is directed to a device for detection of an analyte in a sample by colorimetric optical readout, comprising: (a) a chamber for containing a sample that includes an analyte; and (b) a composition positioned in the chamber, the composition including: (i) a polymer having pores specifically imprinted to provide for capture of the analyte in said pores; (ii) nanoparticles layered on said polymer; and (iii) photochromic optical switch molecules coated on said nanoparticles, wherein capture of the analyte in the pores of the polymer results in a change in the spatial relation of the nanoparticles layered on the polymer, said change in spatial relation of the nanoparticles causing the photochromic optical switch molecules coated thereon to undergo a change in energy state which corresponds to a visible change in optical spectra of said photochromic optical switch molecules, thereby providing detection of the analyte by colorimetric optical readout.

Yet another aspect of the present invention provides a method of detecting an analyte in a sample by colorimetric optical readout, comprising: (a) contacting a sample that includes an analyte with a composition comprising: (i) a polymer having pores specifically imprinted to provide for capture of the analyte in said pores; (ii) nanoparticles layered on said polymer; and (iii) photochromic optical switch molecules coated on said nanoparticles; (b) capturing the analyte in the pores of the polymer; and (c) detecting the analyte, wherein said capture of the analyte results in a change in the spatial relation of the nanoparticles layered on the polymer, said change in spatial relation of the nanoparticles causing the photochromic optical switch molecules coated thereon to undergo a change in energy state which corresponds to a visible change in optical spectra of said photochromic optical switch molecules, thereby providing detection of the analyte by colorimetric optical readout.

The invention further encompasses an article for detecting an analyte in a sample by colorimetric optical readout, said article comprising a composition described and claimed herein, capable of detecting by colorimetric optical readout an analyte contained in a sample contacted with said article.

Of course, the invention also contemplates the use of a composition as described and claimed herein for the manufacture of devices and articles for analyte detection by colorimetric readout as well as the use of the present compositions incorporated into devices and articles for analyte detection by colorimetric readout.

Other objects, features and advantages of the present invention will become apparent after review of the specification, claims and drawings.

DETAILED DESCRIPTION OF THE INVENTION

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Molecularly Imprinted Polymers (MIPs):

Molecular imprinting is a laboratory technique that has been adapted by research laboratories worldwide in recent years. Using the technique, recognition sites can be molded into polymers. The recognition sites mimic the binding sites of natural antibodies in their interaction with a target antigen. Binding constants are as low as 4.0 nmol/L for a small number of well defined sites, and cross-reactivity is similar to or better than those observed with biological antibodies.

Molecular imprinting achieves the formation of reversible covalent or noncovalent interactions between polymerizable monomers, which are then polymerized in the presence of a cross-linking monomer and porogenic solvent, and an imprinting molecule or template. The result is a hard macroporous polymer. Recognition sites, with shape and functional groups complementary to the imprint molecule are then formed by breaking reversible interactions between the polymer and the template. Investigators have shown, using a variety of experimental approaches, that such synthetically produced recognition sites are capable of rebinding the imprint species in preference to other closely related structures.

A variety of monomers have been used in molecular imprinting. In particular, different monomers have been used that are capable of different interaction with imprint molecules. Furthermore, various monomer configurations, such as bulk polymers, beads, membranes, and polymer films have been used in molecular imprinting.

Imprinting with bulk methacrylate polymers containing methacrylic acid is common Such polymers can form either a noncovalent hydrogen bond or ionic interactions with the imprint molecule. The polymerization is performed in a dry organic solvent. Polymers have been prepared with impressive selectivity towards small molecules, including physiologically active drugs. Pharmacological structures that have been successfully imprinted (imprint antigens) include drugs such as Theophylline, Diazepam, Morphine, S-Propranolol and cortisol.

The indicator mechanism of the present invention can operate via any suitable process resulting in a permanent and detectable change in the template or in the indicator (sensor) mechanism. For example, a subsequent polymerization in the presence of a crosslinker, a cross-linking reaction or other process, results in the formation of an insoluble matrix in which the template sites reside. In one example involving steroid detection, a suitable crosslinker is the stilbene moiety that can delocalize the p electrons of steroids templates along with other ring structures.

"Shape" of imprint in MIP and effects of analyte populations:

These "shape" effects override known thermodynamically determined trends operative in "self assembly" models. Thus, it appears that molecular shape and not necessarily molecular structure (linker dependence) is crucially important for analyte recognition in a MIP. As a consequence, increased recognition sites even for templates that lack the specific binding group can achieve a high selectivity based on the recognition of shape (of the MIP) alone.

Figure 3:
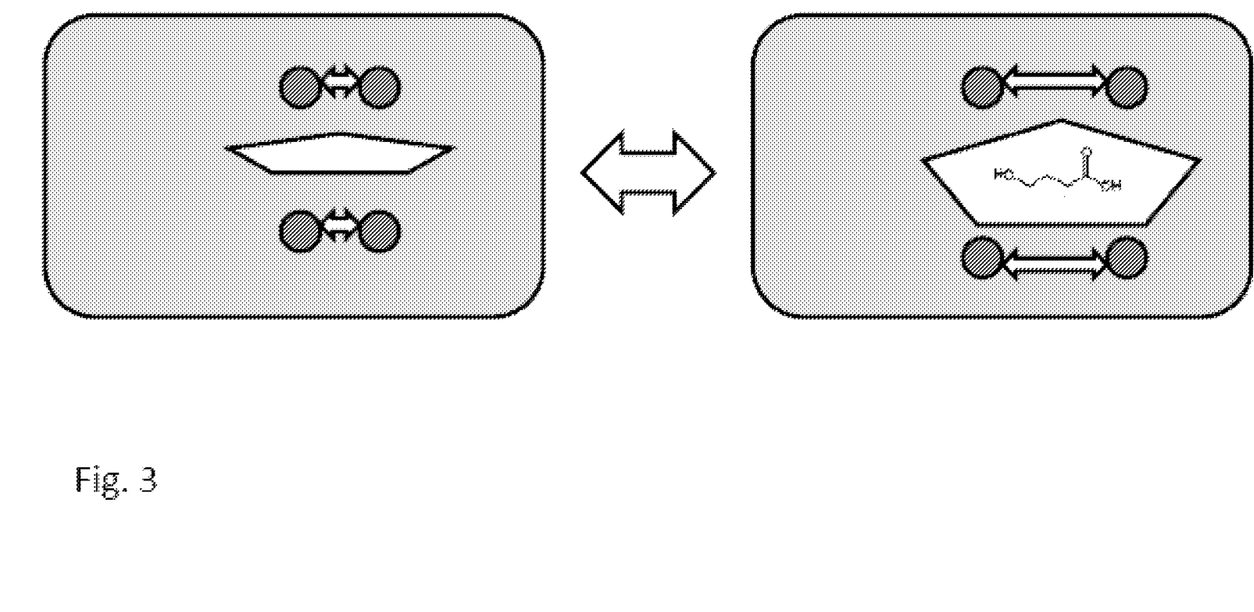
FIG. 3 shows a schematic of analyte occupying pores in a MIP with a resultant effect of changing the spatial relationship between surrounding metal nanoparticles.

Use of nanoparticle detection for MIP shape changes can be done in the presence of an analyte. Detection of molecular shape changes in MIPs in the presence of analyte binding has been investigated by use of resulting spatial differences of immobilized Au nanoparticles in a Au-MIP composite (See, specifically, Diagram 2A-B in the *Anals of Chemistry* article by Matsui, referenced below). FIG. 3 shows an example of a pocket expanding once an analyte enters and the effect of surface molecules. An example of a surface molecule could be gold nano. A family of analytes related to adrenaline altered the physical proximity of Au nano-particles immobilized within an imprinted polymer exhibiting selective binding. This was measured for the non-imprinted polymer, the imprinted polymer and after washout of the analyte. A blue-shift in the plasmon absorption band of the immobilized Au nanoparticles accompanied the swelling using adrenaline as the model analyte as detected by UV-Vis spectro-photometry. Similar plasmon and UV-Vis effects have been reported for metal-colloid mono-layers. It was also shown that molecular imprinting effectively enhanced the sensitivity and selectivity, and accordingly, Au-MIP selectively detected the analyte at 5 µM. The combination of molecular imprinting and the Au nano-particle-based sensing system validates the prior reports of shape dependencies.

The invention is for detection of molecules in a nano microenvironment with a readout in the colorimetric range. The device is composed of a series of components. The components all act in unison with a directionality that is defined by the fundamental thermodynamics and energy transfer allowed by nano particles, the laws governing the self assembly of nano-particles, molecular imprint polymers, colloidal particles and the energy states of photochromic optical switches.

Referring now to FIG. 3, the invention provides in one aspect a biosensor device. The first component is a porous polymer (water insoluble) either in a particulate or mesoporous block monolith form. The polymer is prefabricated with imprint holes throughout. These holes are specific to both the size and shape of the analyte to be detected. Analyte refers to any molecule that the device is utilized for sensing. When the polymer is immersed in any medium containing the desired analyte, there is an irreversible localization of the analytes specifically into the molecular pore (Imprint space). This Imprint space is changed by virtue of the repository of the analyte. The change is appreciated as both a trapping of the analyte within the pore, and additionally the energy consequences of this event.

In the polymer with the analyte imprinted and residing therein there is a resultant change in the shape of the imprint. It becomes larger as a result of being occupied by the analyte. The change in shape results in a net increase in the energy of the binding of the analyte that is transferred directly to the surface (outside) of the polymer.

The outside of the polymer is coated with the novel sensing device of which one embodiment may be noble metals such as gold or silver or elemental nanoparticles. The sensing device is composed of a layer of noble metal nanoparticles which can be layered by more than one technique. Exemplary layering techniques include Nanosphere lithography on the surface, colloidal gold surface coating, plus any other technology utilized to produce a surface of any nano particle affixed to a solid.

The result is that the nano particle application patterns itself according to the thermodynamically predicted behavior encompassing the self assembly of particles in the nano dimension, as well as the co-polymeric, template and linker parts of the MIP. The relation of the position of the nanoparticles is such that they are equidistant from each other (as thermodynamically predicted and accounted for by the theory of Self assembly of Matter). The geographic consequence of the analytes taking up space within the molecular imprinted pores is a detectable change in the distance of the nano particles from each other. This of course is best understood as the transfer of extra energy as defined by a change in the shape of the polymer to the outside of the polymer.

The nano surface particles, self assembled on the surface, are coated with tethered monomer units of photochromic optical switch molecules. The optical switch is a term used to indicate that the addition of energy (motional, vibrational, rotational, positional) acquired by the nano particle as is breaks from the fundamental self assembly positions is transferred immediately to a organic molecule monomer that can occupy two different states. In one state (ground state) the monomer is colorless. With the addition of energy the monomer changes to a different form (absorption of the energy of the nano as received from the change in shape of the imprint). The new configuration of the photochromic molecule is in terms of the delocalization of electrons within its structure. The delocalization give rise to a new energy state that corresponds to the optical spectra hence a bright color is generated. Because the analyte is permanently held within the polymer, the color change is permanent.

In separate experiments it has been shown that when the analytes are removed chemically from the polymer there is a corresponding decrease in the imprint size to that which is even smaller than the original shape (unoccupied). However, because the analyte is bound to the imprint the color change (optical color) is instant and permanent. Because the nano surface population is infinitely large the amplification of the shape change energy coupled with the infinite number of photochromic optical monomers per nano particle guarantees that the increase in color will be more than enough so that the color change is easily identifiable with ordinary conditions, by human sight. No added ultra violet light may be required.

The complexity of these mechanisms parallels the fundamental scientific laws that govern the behavior of the components. These principals includes the laws of molecular and nano self assembly and the stochastic effects of single molecule energy wavelength line shapes (as additive), and have been further proven by advances in the mathematics, physics and thermodynamics of energy capturing as applied to the photochromic switches and the properties of the copolymer structures that the sensing device is being applied to.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Molecular Imprinting Polymers can be created using a range of syntheses known in the field. A general method for preparation of polymers is as follows: The imprinted polymer (A) can be prepared by co-polymerization of a cross-linking monomer (such as EDMA) with a functional monomer (such as 4-VP) in the presence of the template. Given that the goal is to prepare and use the imprinted polymers in water-containing solvents, complex formation relies on hydrophobic and ionic interactions which, unlike hydrogen bonding, are not (or are at least to a lesser extent) disturbed in the presence of water. The selection of 4-VP as the functional monomer allows for ionic interaction with the carboxyl group of the template as well as using the hydrophobicity of its aromatic ring. The imprinting is preferably performed in methanol/water (4:1) since EDMA and the template would be only poorly soluble in pure water.

For the imprinted polymer (A), 20 mmol of EDMA, 4 mmol of 4-VP, 1 mmol of (template), and 0.31 mmol of polymerization initiator (ABDV) are weighed into glass test tubes and dissolved in 4 mL of methanol and 1 mL of ultra-pure water. The solutions are then sonicated, sparged with nitrogen for 2 minutes, and placed in a thermostated water bath at 45° C. for 4 hours, followed by 2 hours at 60° C.

Control polymers are prepared using the same recipe, but without the addition of the template (B), or alternately containing 1 mmol of toluene and 1 mmol of acetic acid (C) or 1 mmol of POEtOH (D) instead of the template.

The resultant hard bulk polymers are ground in a mechanical mortar and wet-sieved in acetone through a 25-µm sieve.

The particles are washed by incubation in methanol/acetic acid (7:3) (2×), acetonitrile/acetic acid (9:1) (2×), acetonitrile (1×), and methanol (2×) for 2 hours each time, followed by centrifugation.

The particles are then re-suspended in acetone and allowed to settle for 4 hours. The particles that remain in suspension (fines) are collected, and the procedure is repeated four times. The solvent is removed by centrifugation, and the particles dried in vacuo. In this way, fine particles are obtained with a total yield of 60%. These particles should have an average diameter of 1 µm (determined by transmission electron microscopy). The porosity of the particles may be determined by nitrogen adsorption/desorption porosimetry on a Micrometrix ASAP 2400M instrument (Atlanta, Ga.).

Example 2

Preparation of controlled size Au Nano colloid preparation. To create an Au nano colloid preparation, we anticipate a modification of the procedures of Matsui, as well as other similar procedures. The following exemplary reagents may be used: Acrylic acid, 2-aminoethanol hydrochloride, 2,2'-azobis(isobutyronitrile) (AIBN), chloroform, dimethyl sulfoxide (DMSO), tetraoctylammonium bromide (TOAB), toluene, hydrogen tetrachloroaurate(III (HAuCl$_4$.4H$_2$O), 11-mercaptoundecanoic acid (MUA) and sodium borohydride, N,N methylenebis(acrylamide) (MBA), and N-isopropylacrylamide (NIPA). Toluene, DMSO, and acrylic acid should be purified by distillation, and MBA and AIBN should be purified by recrystallization prior to use. All other reagents should be used without further purification.

Example 3

The Preparation of Size-Controlled Au Nanoparticles. This preparation may be carried out according to reported and modified methods. A solution of TOAB (3.3 g, 6.0 mmol) in toluene (400 mL) is added to an aqueous solution of HAuCl$_4$.4H$_2$O (15 mM, 200 mL, 3.0 mmol). A solution of MUA (655 mg, 3.0 mmol) in toluene (100 mL) is then gradually added to the resulting mixture while vigorously stirring, followed by the drop wise addition of a freshly prepared aqueous solution of NaBH$_4$ (0.30 M, 100 mL, 30 mmol). After the mixture is stirred for 1 h, the organic phase is separated and washed with distilled water. The solvent is then completely evaporated in a rotary evaporator and dried in vacuo for 1 day. The black solid thus obtained is then heat treated at 155° C. at the heating rate of 2° C. min-1 for 30 min. The heat-treated product is then dissolved in 50 mL of toluene, mixed with 800 mL of chloroform to remove the excess TOAB and MUA, and then filtered to give the Au nanoparticles.

Example 4

The Colloid Preparation. Au Colloid Nano particles may be based on common methods in the literature, with certain modifications. All glassware used should be cleaned in aqua regia (3 parts HCl, 1 part HN0$_3$), rinsed in triply distilled H$_2$O, and oven-dried prior to use. The following stock solutions require the use of triply distilled H$_2$O filtered through a 0.8 µm membrane filter (Gelman Scientific): 1% HAuCL, 38.8 mM sodium citrate, and 1% sodium citrate. Other solutions should be made fresh as needed and should also use triply distilled, filtered H$_2$O. Two typical Au preparations are set forth below.

Preparation I. In a 1 L round-bottom flask equipped with a condenser, 500 mL of 1 mM HAuCl is brought to a rolling boil with vigorous stirring. Rapid addition of 50 mL of 38.8 mM sodium citrate to the vortex of the solution will result in a color change from pale yellow to burgundy. Boiling is continued for 10 min; the heating mantle is then removed, and stirring is continued for an additional 15 min. After the solution reaches room temperature, it is filtered through a 0.8 um Gelman membrane filter. The resulting solution of colloidal particles can be characterized by an absorption maximum at 520 nm. Transmission electron microscopy (TEM) indicates a particle size of 13 nm 1.7 nm (100 particles sampled).

Preparation II. In a 1 L round-bottom flask equipped with a condenser, 500 mL of 0.01% HAuCl is brought to a boil with vigorous stirring. To this solution, 7.5 mL of 1% sodium citrate is added. The solution turns blue within 25 s; the final color change to red-violet occurs about 70 s later. Boiling continues for an additional 10 min, the heating source is removed, and the colloid is stirred for another 15 min. TEM data should indicates an average diameter of 18 nm 4.6 nm (89 particles sampled). Particle diameter can be varied by adding larger or smaller amounts of sodium citrate to decrease or increase the particle size, respectively.

Ag colloid is prepared according to the method of Lee and Meisel. Using a heating plate and a 1 L flask, a solution of 90 mg AgNO$_3$ in 500 mL of triply distilled H$_2$O is brought to boiling with rapid stirring. To this solution is added 10 mL of 1% sodium citrate. Boiling is continued for 30 min, after which time the flask is removed from the heat source, and the solution is diluted with triply distilled H$_2$O to obtain a final volume of 420 mL. All colloids should be stored at room temperature in dark bottles and should be generally used within 1-2 months after preparation. Samples for particle sizing by TEM can be prepared by drop coating 10 pL of the colloid onto a Formvar-coated Cu grid and allowing the sample to dry. Average sizes are determined by measuring diameters along a consistent axis throughout the sample.

Example 5

Surface Derivatization. Substrates should be cleaned prior to derivatization as follows: glass and quartz, cut to dimensions of approximately 2 cm×0.7 cm, are cleaned for 10 min in a bath consisting of 4 parts H$_2$SO$_4$ to 1 part 30% H$_2$O$_2$ at 60° C. The samples are rinsed in spectrophotometric grade CH$_3$OH and stored in this solvent until needed. SiO coated TEM grids are cleaned in ozone plasma for 30 min. Cleaning often should precede use of the grids by several weeks; during this period, the grids should be stored in TEM grid holders in air.

Derivatization of glass and quartz substrates with alkoxysilanes is accomplished in the following manner. Clean substrates are submerged into vials of silane diluted 1:4 with spectrophotometric grade CH$_3$OH. After 24 hours, the substrates are removed and rinsed profusely with CH$_3$OH to remove unbound monomer from the surface. At this point, silanized substrates are stored in CH$_3$OH until needed. Prior to derivatization with colloidal Au, the substrates are rinsed with H$_2$O; they are then immersed in vials of colloidal Au for 24 h. A final H$_2$O rinse concludes the derivatization process. Similarly, carboxyl-terminated SAMs prepared on Au-coated silicon substrates are immersed in colloidal Au solutions for several days. The substrates are stored in H$_2$O until needed for analysis.

Due to their inherent fragility and small size, greater care is required for the derivatization of TEM grids. Specifically, the SiO coated TEM grids are immersed in neat silane for 3 hours, followed by extensive methanol rinses and a $H_2O$ rinse. The rinsing is accomplished by pipetting solvent across the grid surface or by swishing the grid back and forth in a vial of solvent. Effort should be made to minimize the solvent flow perpendicular to the grid face in order to better preserve the Formvar film. Finally, the grids are floated on a colloid solution for 12 hours. Samples are rinsed with $H_2O$ and allowed to air-dry on filter paper prior to analysis.

Example 6

Colorimetric Gold Nanoparticles as optical sensors of bimolecular interactions. The methods of proving that self assembled Au nano gives a change in the absorption spectrum (UV-Vis) of a self assembled monolayer of colloidal gold on glass as a function of the biomolecular binding to the surface of the immobilized colloids are based on the methods reported in the literature.

Figure 1:
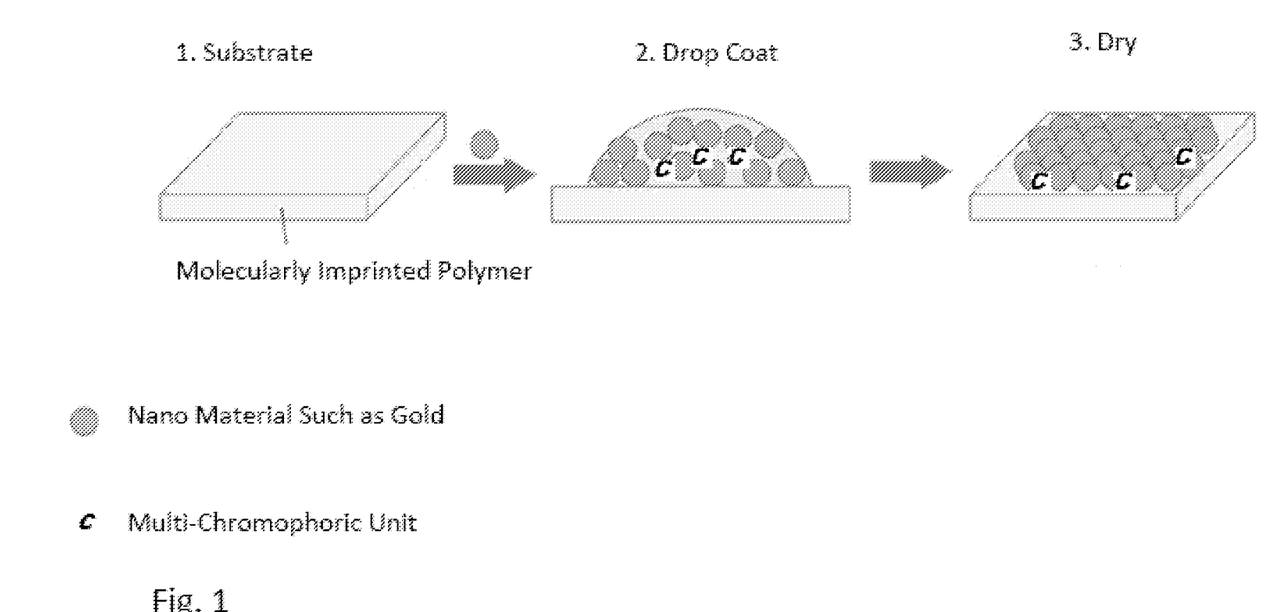
FIG. 1 depicts a general procedure for layering a mixture of metal nanoparticles and a chromophore onto the surface of a molecularly imprinted polymer ("MIP").
Figure 2:
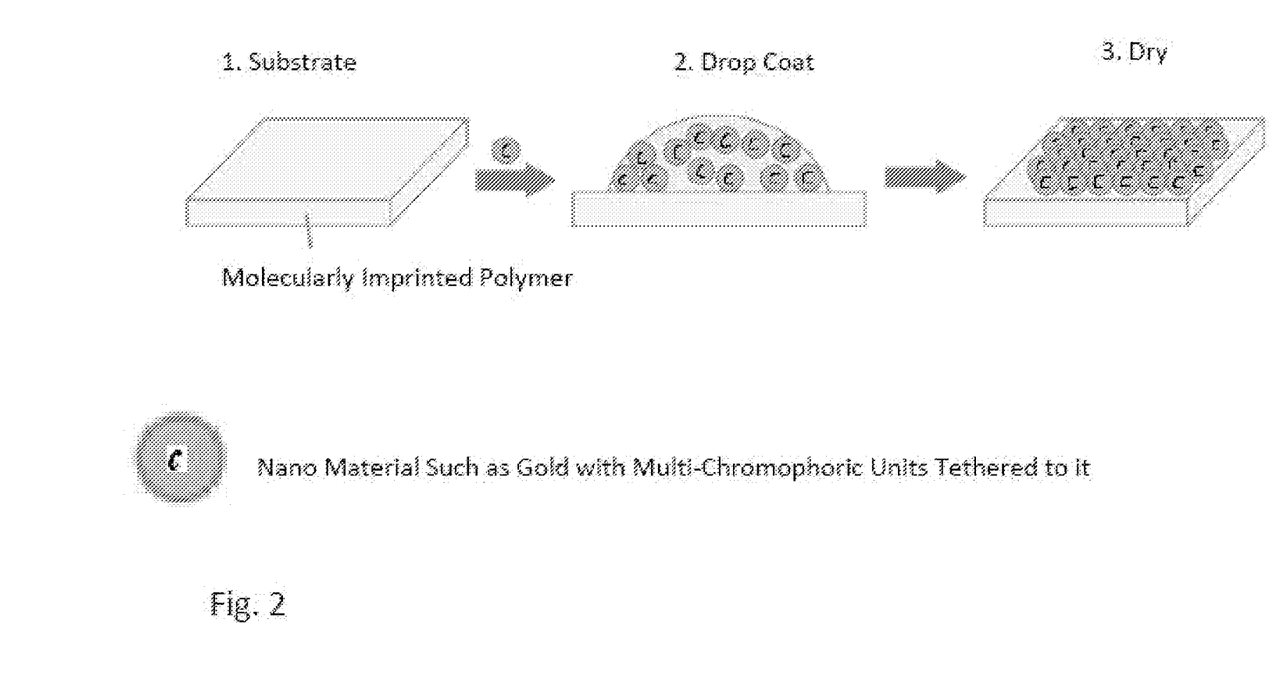
FIG. 2 illustrates an alternative procedure for layering chromophore-labeled metal nanoparticles onto the surface of a MIP.

Nanoparticles can be layered onto a MIP using multiple techniques, one embodiment of which is nanosphere lithography. Another embodiment could use a mixture of nanoparticles which include chromophores and gold or chromophores tethered to gold that self assemble, as shown in FIG. 1 and FIG. 2.

Plasmon Resonance measurements have been used extensively to investigate polymer and biopolymer exhorbtion onto gold films with applications to biosensors.

Example 7

Tethering of Photochromic switches onto Gold Nanocolloids and Photochromic Switches. Reversible interconversion between the colorless and colored forms of photochromic compounds can be exploited to modulate electron and energy transfer processes. A photochrome can be designed to accept electrons or energy from a complementary donor in one of its two states only.

Alternatively, the photoinduced transformations associated with a photochromic switch can be engineered to control the relative orientation and distance of donor-acceptor pairs. The photo-regulated transfer of energy or electrons results in the modulation of the emission intensity.

Development of newer optical switch reagents whose interactions and activities within a bioconjugate can be rapidly, reversibly, and efficiently modulated with light has been reported. This new approach exploits the properties of photochromic probes that undergo rapid and reversible, light-directed transitions between a colorless, weakly polarized spiro (SP) state and a colorful and highly polarized merocyanine (MC) state. Excitation of SP at 365 nm light generates MC, while excitation of MC at 546 nm generates SP.

These newer monomer molecular optical photochromic switches can also be specifically labeled to a biomolecule. An example could be found by taking the time to examine the family of photochromic monomer probes that harbor maleimide, bromomethyl, or iodomethyl groups that can undergo selective labeling of thiol groups of biomolecules or colloidal nanoparticles that have been functionalized. This new class of monomeric photochromic switches has significant advantages over traditional protein labeled photochromes (in protein conjugates) which exhibit complex photochemistry, form dimers that have different optical properties compared to the monomer, and exhibit complex and irreversible photochemistry.

Example 8

Functionalization of the Gold Colloids. The fabrication and characterization of colloidal gold monolayer on glass ($Au_{CM}$) can be done by multiple methods.

The following methods are based on standard literature methods. Glass coverslips (VWR Scientific) cut into 10×50 mm pieces can be used as the substrate for assembly of the colloidal gold monolayers. The glass substrates are cleaned by sonication for 5 min in hot RBS 35 detergent (Pierce) and washed extensively with distilled water. The substrate is further cleaned in a 1:1 solution of methanol and HCl for 30 min, washed extensively with distilled water, and dried overnight at 60° C. The cleaned glass substrates are immersed in a 10% (v/v) solution of γ-(aminopropyl)triethoxysilane (APTES, Sigma) in anhydrous ethanol for 15 min, rinsed five times in ethanol with sonication, and dried at 120° C. for 3 h. The silanized glass coverslips are subsequently immersed overnight in a colloidal gold solution (11.6 nM) to form a self-assembled monolayer of the gold colloids on both sides of the glass coverslip ($Au_{CM}$). The immobilized colloids can be imaged by atomic force microscopy (AFM) in tapping mode in air using standard $Si_3N_4$ cantilevers on a Multimode Nanoscope IIIa (Digital Instruments Inc.).

The following methods can be utilized to create functionalization of $Au_{CM}$. $Au_{CM}$ is modified by the formation of a self-assembled monolayer (SAM) of mercaptopropionic acid (MPA) by incubation of the colloid monolayer on glass in a 1 mM solution of MPA in absolute ethanol for 10 min at room temperature (termed $Au_{CM}$-MPA). These samples can be used for fibrinogen adsorption studies. $Au_{CM}$-MPA samples are functionalized with biotin as follows. $Au_{CM}$-MPA samples are immersed in an ethanol solution of 0.1 M 1-ethyl-3-(3-dimethylaminopropyl)carbodiimide (EDAC, Sigma) and 0.2 M pentafluorophenol (PFP, Sigma) for 20 min at room temperature, rinsed three times with ethanol, immersed in a 100 μg/mL solution of (+)-biotinyl-3,6,9-trioxaundecanediamine (trade name, EZ-Link-biotin-PEO-LC-amine; Pierce) in ethanol for 2 h, washed with ethanol, and stored in PBS at 4° C. until further use.

Absorbance Measurements of Immobilized Gold Colloids can be taken on glass or other substrates. A temperature-controlled spectrophotometer (Cary 300Bio, Varian Instruments) can be used to measure the absorbance of the immobilized gold colloids on glass coverslips. A rectangular glass flow cell of 4 mm width can be designed in-house to hold the samples. Samples are positioned in the center of the glass cell using two Teflon guides on top of the cell. Spectra are collected in transmission mode over a range of 350-850 nm. The glass coverslips are scanned using a commercial UMAX Super Vista S-12 flatbed scanner (UMAX Technologies, Inc.). The color image are converted to gray scale in NIH Image and analyzed for mean and standard deviation. The data can be analyzed by one-way ANOVA and Bonferroni multiple comparison test using InStat for MacIntosh version 2.0 (GraphPad Software, Inc., San Diego, Calif.).

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

REFERENCES

JACS (2007) 129: 15911-15918.
JACS (2004) 126: 7827-7833 and Analyst (2001) 126: 793-797.
Langmuir (2003) 19: 3921-3925.
Anal Chem (2004) 76: 1310-1315 and Int Reviews in Physical Chemistry (2000) 19:409-413.
Anal Chem (2004) 76: 1310-1315.
Science (1995) 267:1629-1632, Langmuir (2001) 17: 957-960, J. Am Chem Soc. (2001) 123: 3177-3178, Optics Lett (2000) 25: 372-374, Anal Chem (1995) 67: 735-743, Langmuir (1995) 11: 1313-1317.
K. Mosbach, O. Ramstrom, Biol. and Technol. 14 (1996) 163.
G. Wulff, Angew. Chem., Int. Ed. Engl. 34 (1995) 1812.
K. J. Shea, Trends Polym. Sci. 2 (1994) 166.
G. Vlatakis, L. I. Andersson, R. Müller, K. Mosbach, Nature 361 (1993) 645.
Haupt K, Dzgoev A, Mosbach K. Anal Chem (1998) 70: 628-631.
Analytic Chemistry (2004) 76: 1310-1315), Akamatsu K et. Al., J. Material Chemistry (2002) 12: 2862-2865), Grabar K C et al. (Anal Chemistry (1995) 67: 735-743), Frens G. (Nature Phys Sci (1973) 241: 20-22), Sutherland et al J. Colloid Interface Sci (1992) 48: 129-141.
Matsui et. al. Analytic Chemistry (2004) 76: 1310-1315.
Akamatsu K et. al. J. Material Chemistry (2002) 12: 2862-2865. Grabar K C et al. Anal Chemistry (1995) 67: 735-743.
Frens G. Nature Phys Sci (1973) 241: 20-22.
Sutherland et al J. Colloid Interface Sci (1992) 48: 129-141.
Eck D, Helm, C A Wagner N J, Vaynberg K A. Plasmon Resonance Measurement of the Adsorption and Adsorption Kinetics of a Biopolymer onto Gold Nanocolloids. Langmuir (2001) 17: 957-960.
Nath N, Chikoti A. A colorimetric Gold Nanoparticle Sensor to interrogate Biomolecular Interactions in real time on a surface. Anal Chem (2002) 74: 504-509.
Lyon, L. A.; Pena, D. J.; Natan, M. J. Surface Plasmon resonance of an au colloid-modified au films: particle size dependence. J. Phys. CHem, B 1999, 103, 5826-5831.
Katherine A. Willets and Richard P. Van Duyne, Localized Surface Plasmon Resonance Spectroscopy and sensing, annual review of physical chemistry 2007. 58: 267-297.
Raymo F M, Tomasulo M. Electron and Energy transfer modulation with photochromic switches. Chem Soc Rev. (2005) 34: 327-336.
Sakata T, Yan Y, Marriott G. Family of Site Selective Molecular Optical Switches. J. Org Chem (2005) 70: 2009-2013.
Medintz I L et al. J. Am. Chem. Soc (2004) 126: 30-31.
Angelini N et. Al. Biophys J. (1998) 74: 2601-2610.
Song. L. et al. Photochem. Photobiol A. (2002) 150: 177-185.
Nath N, Chilkoti A. A Colorimetric Gold Nanoparticle Sensor to Interrogate Biomolecular Interactions in Real time on a surface. Anal Chem (2002) 74: 504-509.
Sato T, Hasko D G, Ahmed H. Nanoscale Colloidal Particles: Monolayer organization and Patterning. J. Vasc Sci Technol B (1997) 15: 45-48.

What is claimed is:

1. A composition for use in detecting an analyte in a sample by colorimetric optical readout, comprising:
   (a) a polymer having pores specifically imprinted to provide for capture of an analyte in said pores;
   (b) nanoparticles layered on said polymer; and
   (c) photochromic optical switch molecules coated on said nanoparticles,
   wherein capture of the analyte in the pores of the polymer results in a change in the spatial relation of the nanoparticles layered on the polymer, said change in spatial relation of the nanoparticles causing the photochromic optical switch molecules coated thereon to undergo a change in energy state which corresponds to a visible change in optical spectra of said photochromic optical switch molecules, thereby providing detection of the analyte by colorimetric optical readout.

2. A device for detection of an analyte in a sample by colorimetric optical readout, comprising:
   (a) a chamber for containing a sample that includes an analyte; and
   (b) a composition positioned in the chamber, the composition including:
      (i) a polymer having pores specifically imprinted to provide for capture of the analyte in said pores;
      (ii) nanoparticles layered on said polymer; and
      (iii) photochromic optical switch molecules coated on said nanoparticles,
   wherein capture of the analyte in the pores of the polymer results in a change in the spatial relation of the nanoparticles layered on the polymer, said change in spatial relation of the nanoparticles causing the photochromic optical switch molecules coated thereon to undergo a change in energy state which corresponds to a visible change in optical spectra of said photochromic optical switch molecules, thereby providing detection of the analyte by colorimetric optical readout.

3. A method of detecting an analyte in a sample by colorimetric optical readout, comprising:
   (a) contacting a sample that includes an analyte with a composition comprising:
      (i) a polymer having pores specifically imprinted to provide for capture of the analyte in said pores;
      (ii) nanoparticles layered on said polymer; and
      (iii) photochromic optical switch molecules coated on said nanoparticles;
   (b) capturing the analyte in the pores of the polymer; and
   (c) detecting the analyte,
   wherein said capture of the analyte results in a change in the spatial relation of the nanoparticles layered on the polymer, said change in spatial relation of the nanoparticles causing the photochromic optical switch molecules coated thereon to undergo a change in energy state which corresponds to a visible change in optical spectra of said photochromic optical switch molecules, thereby providing detection of the analyte by colorimetric optical readout.

4. An article for detecting an analyte in a sample by colorimetric optical readout, said article comprising a composition according to claim 1 capable of detecting by colorimetric optical readout an analyte contained in a sample contacted with said article.

5. A composition according to claim 1 for use in detecting an analyte by colorimetric optical readout.

* * * * *